US00PP11552P

United States Patent [19]

Armitage

[11] Patent Number: Plant 11,552

[45] Date of Patent: Oct. 10, 2000

[54] ROSEMARY PLANT NAMED 'ATHENS BLUE SPIRES'

[75] Inventor: Allan M. Armitage, Athens, Ga.

[73] Assignee: University of Georgia Research Foundation, Inc., Athens, Ga.

[21] Appl. No.: 09/105,816

[22] Filed: Jun. 26, 1998

[51] Int. Cl.[7] ..... A01H 5/00

[52] U.S. Cl. ..... Plt./258

[58] Field of Search ..... Plt./258, 226, 373

[56] References Cited

U.S. PATENT DOCUMENTS

P.P. 9,124 5/1995 Johnson ..... Plt./226

P.P. 10,308 3/1998 Wolters et al. ..... Plt./258

*Primary Examiner*—Howard J. Locker
*Assistant Examiner*—Wendy A. Baker
*Attorney, Agent, or Firm*—Needle & Rosenberg, P.C.

[57] ABSTRACT

A new and distinct cultivar of rosemary plant, *Rosmarinus officinalis,* named 'Athens Blue Spires', was selected from a commercial rosemary seed package. The origin of the new cultivar is otherwise unknown. The new cultivar is distinguished by the unique combination of the following traits: good cold hardiness, lavender blue flowers, extensive self-branching and an upright habit, small-sized, narrow-shaped foliage, and vigorous growth. The cultivar demonstrates good disease tolerance and is well-suited for ornamental and culinary uses.

2 Drawing Sheets

SUMMARY OF THE INVENTION

The present invention comprises a new and distinct plant cultivar of *Rosmarinus officinalis* which has been given the name 'Athens Blue Spires'. The following traits have been repeatedly observed and are the most pronounced characteristics of this new cultivar when grown in Georgia, and in combination they distinguish it from existing cultivars:

1. Cold hardiness;
2. Lavender blue flowers;
3. Extensive self-branching and upright habit;
4. small-sized, narrow-shaped foliage; and
5. Rapid, vigorous growth with disease tolerance.

DETAILED DESCRIPTION

Background of the Invention

The rosemary plant, *Rosmarinus officinalis,* is a well-known shrub that is grown for both ornamental use and as a culinary herb.

Origin of the Invention

The plant of this invention was selected at the University of Georgia Horticulture Department trial grounds in Ahtens, Clarke County, Ga., U.S.A. It was selected from a planting of a commercial package of rosemary seeds which were germinated arouund 1988. All other seedlings from the package dies as result of cold or wet exposure during the subsequent winters or as a result of the heat and drought of the subsequent summers. The surviving selection has been named 'Athens Blue Spires'.

Method of Asexual Reproduction

'Athens Blue Spires' was asexually reproduced by the inventor, Dr. Allan Armitage, by rooted cuttings at the Department of Horticulture, University of Georgia, Athens, Ga., U.S.A. This asexual reproduction established that succeeding generations retain all characteristics of the orginal plant as described herein. Asexual reproduction by rooted cuttings has been repeatedly performed both in Athens and at the Center for Applied Nursery Research near Deering, Ga.

Plant Characteristics

In the following description, color references are made to The Royal Horticultural Society Colour Chart (herein "R.H.S.") except where general terms of ordinary dictionary significance are used.

Figure 1:
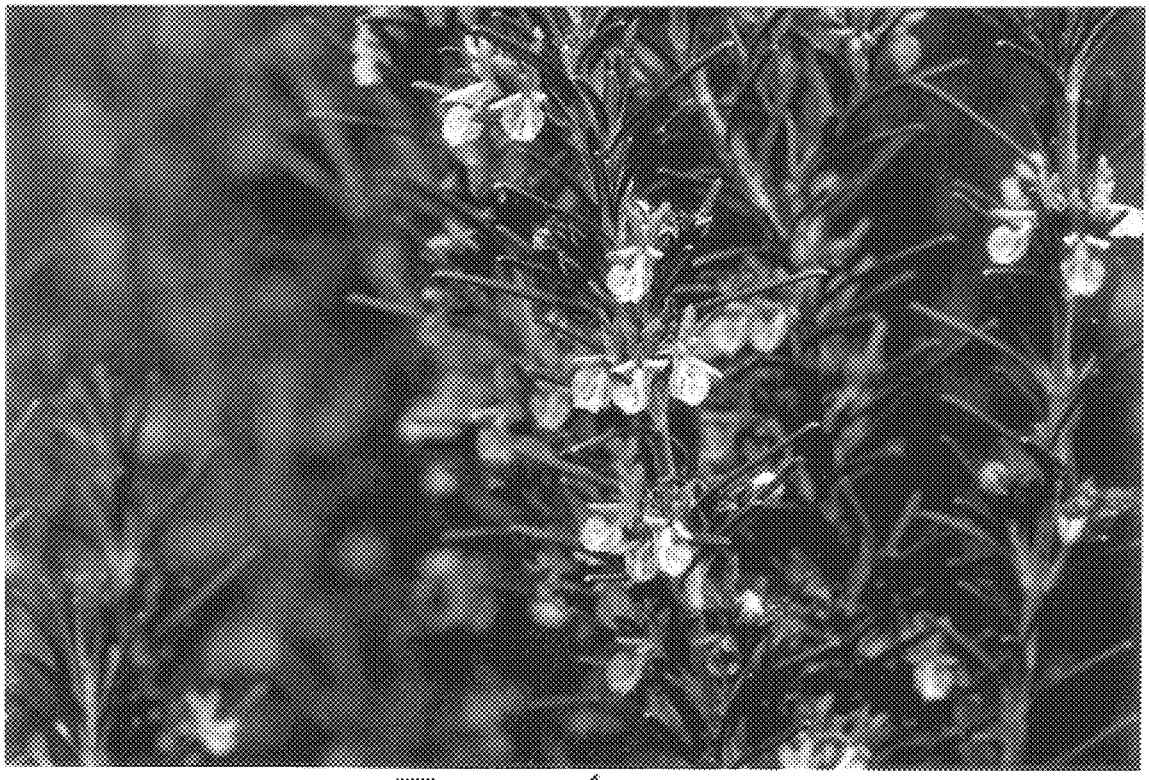
FIG. 1, shows a portion of a typical inflorescence of a mature plant of 'Athens Blue Spires'.
Figure 2:
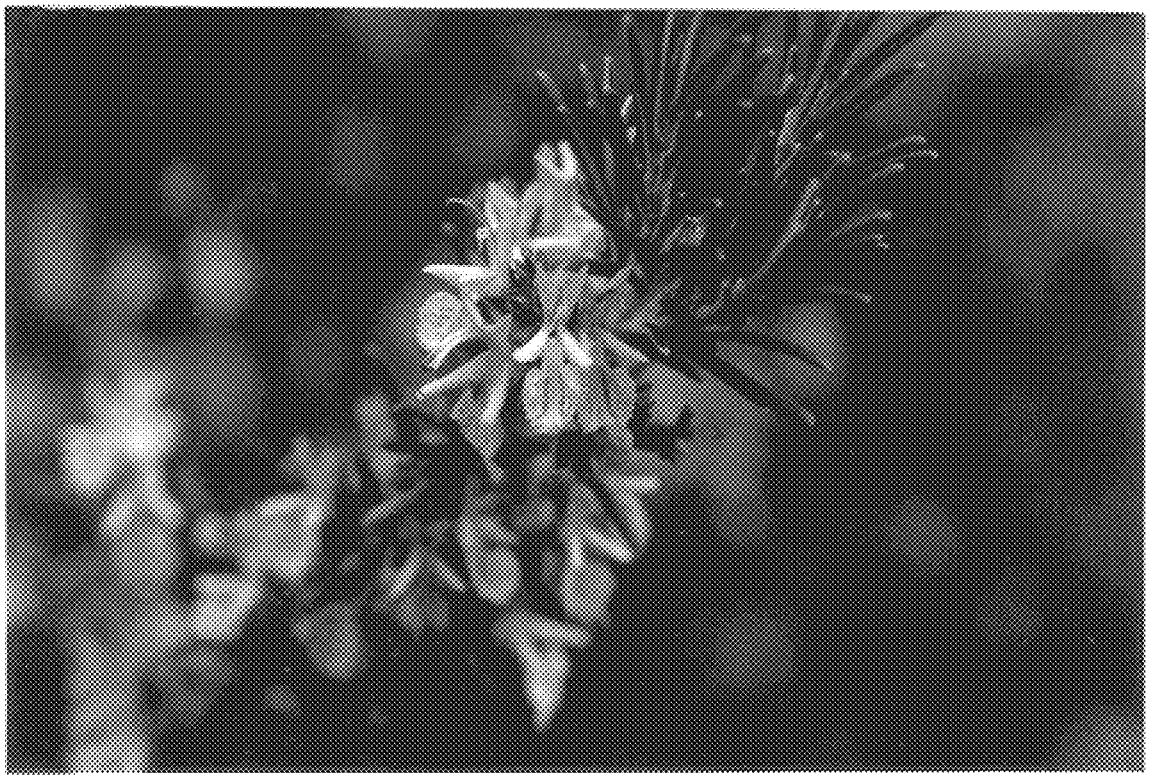
FIG. 2, shows the distinctive flowers of 'Athens Blue Spires'.
Figure 3:
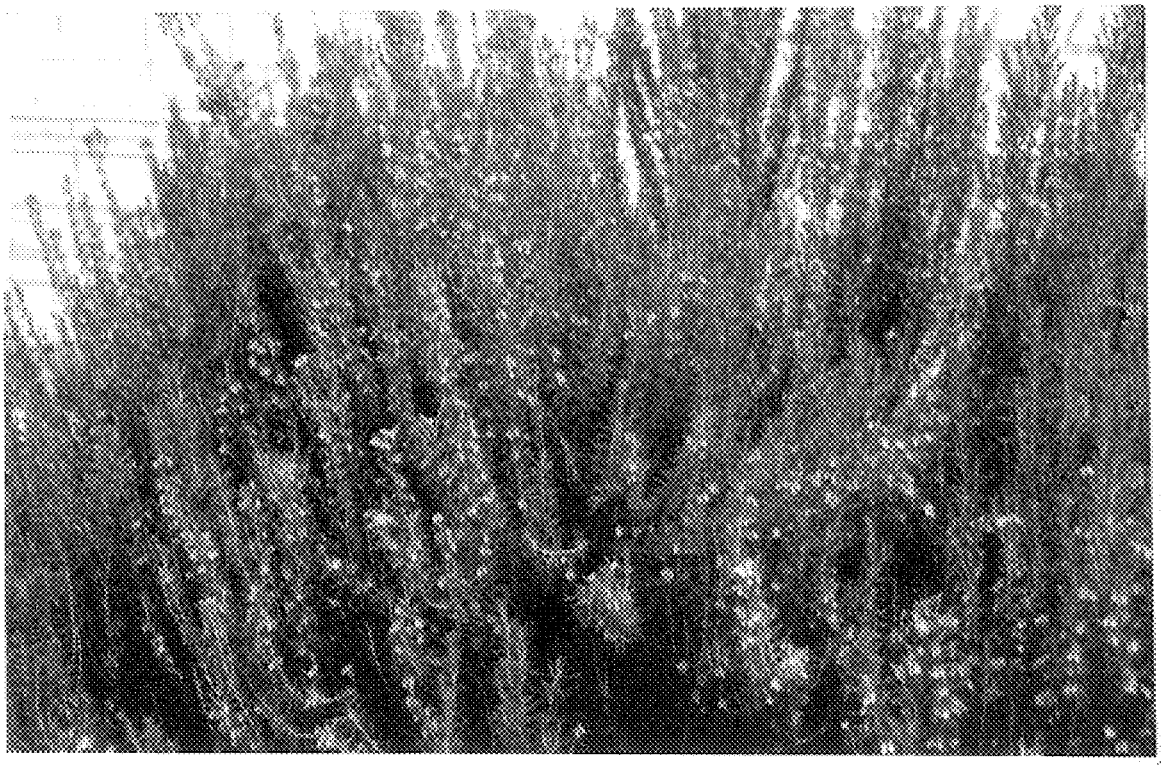
FIG. 3, shows a typical specimen of the entire plant, showing particularly the growth habit, with extensive self-branching and foliage.

Generally, 'Athens Blue Spires' is an upright woody shrub, with round stems and acuminate leaves thath are highly aromatic, that typically grows to a height of 5–6 feet at maturity in Georgia. It is distinguished from other known rosemary cultivars by the combination of its flower color, the narrow structure of its leaves, its cold tolerance, its extensive self-branching, and extremely rapid growth capabilities. As shown in FIG. 3, the excellent self-branching growth habit results in a densely-leaved, thick shrub.

Stems: The stems are woody at the base, while the new growth is silvery white. The mature stem color is in the gray-brown group, R.H.S. 199B. The new growth stem color is in the green group, R.H.S. 147D.

Leaves: The leaves have an alternate arrangement on the stems. They are linear, with an entire, revolute margin. The upper surface is glandular punctate, and the lower surface is densely covered with short, white trichomes. The average leaf length is 0.75 inch and the average width is 1/16 inch (based on an average of five independent measurements). Table 1 presents a comparison of the leave size of 'Athens Blue Spires' with other rosemary cultivars, namely 'Beneton Blue', (unpatented), 'Tuscan Blue', (unpatented), 'Arp', (unpatented), and 'Gorizia', (unpatented).

*Color.*—The colors of the leaves are as follows: upper leaf surface, R.H.S. 137A; center of lower leaf surface, R.H.S. 147D; margins of lower leaf, R.H.S. 137A.

*Fragrance.*—The foliage has the strong aromatic smell typical of the species.

Flower:

*Inflorescence type.*—The flowers are produced in few-flowered verticillasters, arranged in short axillary racemes, which averages 2–4 inches in length. The calyx of each flower is 4-lobed, fused, approximately 0.5 cm in length. The corolla is 2-lipped; the upper lip being concave, approximately 0.6 cm, and 2-lobed, with each lobe linear-acuminate, and lower lip approximately 0.8 cm, and 3-lobed, with the bottom lobe ovate (approximately 0.4 cm wide) and the side lobes linear.

*Timing.*—Flowers are produced from December through April in Georgia. The longevity of an individual flower ranges between 2 days and one week, depending on the temperature.

*Color.*—The pedicel is in the green group, R.H.S. 138B. The calyx is green, R.H.S. 138B. The corolla is lavender (R.H.S. 97C), with the prominent darker blue flecks (R.H.S. 97A), and a band of white (155D) on the lower lip. Table 1 presents a comparison of the flower color of 'Athens Blue Spires' with other rosemary cultivars.

*Reproductive organs.*—Each flower has two stamens, strongly exserted and approximately 1 cm long. The pistil is strongly exserted, linear, and approximately 1.2 cm long. No fruit or seed have been observed on this plant.

TABLE 1

Leaf Size and Flower Color for selected rosemary cultivars

| Cultivar Name | Leaf Size length × width (in inches) | Flower color (per RHS color chart) |
|---|---|---|
| Athens Blue Spires | ¾ × 1/16 | 97C, flecks of 97A, with band of 155D on lower lip |

TABLE 1-continued

Leaf Size and Flower Color for selected rosemary cultivars

| Cultivar Name | Leaf Size length × width (in inches) | Flower color (per RHS color chart) |
|---|---|---|
| Beneton Blue | 1 × ¼ | 155D, with prominent specks of 94A, and marking on lower lip of 90B |
| Tuscan Blue | 1 × ¼ | all 155D, except for specks of 91A on lower lip |
| Arp | 1¼ × ⅛ | all 155D, except for specks of 91A on lower lip |
| Gorizia | 1 × ⅛ | 97C, flecks of 92A, with band of 155D on lower lip |

Other Characteristics

The original and progeny plants have been observed over many growing seasons, and no unusual disease or insect susceptibility has been noted. In Georgia, typical insects include the three spotted spider mite and the Western flower thrips, while typical disease pathogens are root rot pathogens. No susceptibility of 'Athens Blue Spires' to any of these insects or pathogens has been observed. 'Athens Blue Spires' is an extraordinarily vigorous cultivar, growing approximately 18 inches tall and equally wide from a single terminal cutting in a nine month period. Plants placed in outdoor beds doubled in size within the first year, which is more vigorous that any other rosemary cultivar. For example, when grown in pots, 'Athens Blue Spires' grew much more vigorously than rosemary cultivars Beneton Blue, Tuscan Blue, Arp or Gorizia.

'Athens Blue Spires' also has excellent cold tolerance, as measured by observations of the plant over ten years, during which the temperature was as low as 5° F., and yet no damage to the plant was noted.

I claim:

1. A new and distinct *Rosmarinus officinalis* plant that is characterized by a unique combination of upright growth habit, extensive self-branching, lavender-colored flowers, extremely narrow leaves, and excellent cold hardiness, as herein illustrated and described.

* * * * *